(12) United States Patent
Rand (10) Patent No.: US 11,104,947 B2
(45) Date of Patent: Aug. 31, 2021

(54) NANOPORE SEQUENCING OF POLYNUCLEOTIDES WITH MULTIPLE PASSES

(71) Applicant: The Regents of the University of California, Oakland, CA (US)

(72) Inventor: Arthur Rand, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 13 days.

(21) Appl. No.: 16/552,922

(22) Filed: Aug. 27, 2019

(65) Prior Publication Data

US 2020/0002760 A1    Jan. 2, 2020

Related U.S. Application Data (62) Division of application No. 15/515,012, filed as application No. PCT/US2015/052698 on Sep. 28, 2015, now Pat. No. 10,421,998.

(60) Provisional application No. 62/056,963, filed on Sep. 29, 2014.

(51) Int. Cl.
    *C12Q 1/6869* (2018.01)

(52) U.S. Cl.
    CPC ................. *C12Q 1/6869* (2013.01)

(58) Field of Classification Search
    CPC ............ C12Q 1/6869; G01N 33/48721
    See application file for complete search history.

(56) References Cited

FOREIGN PATENT DOCUMENTS

| WO | 2013014451 | 1/2013 |
|---|---|---|
| WO | 2014072703 | 5/2014 |

OTHER PUBLICATIONS

Cherf et al., "Automated forward and reverse ratcheting of DNA in a nanopore at 5-A precision," Nature Biotechnology (2012) 30(4):1344-348.
Laszlo et al., "Detection and mapping of 5-methylcytosine and 5-hydroxymethylcytosine with nanopore MspA," PNAS (2013) 110(47):18904-10909.
Schreiber et al., "Error rates for nanopore discrimination among cytosine, methylcytosine, and hydroxymethylcytosine along individual DNA strands," PNAS (2013) 110(47):18910-18915.
Shim and Gu, "Single-molecule investigation of G-quadruplex using a nanopore sensor," Methods (2012) 57:40-46.

*Primary Examiner* — Joseph G. Dauner
(74) *Attorney, Agent, or Firm* — Brian E. Davy; Bozicevic, Field & Francis LLP (57) ABSTRACT

Provided are methods for analyzing properties of a target portion of a polynucleotide using a nanopore. Also provided are methods for nanopore-based analysis of a polynucleotide, the methods comprising modifying a polynucleotide to comprise an enzyme binding site, an enzyme activity blocking structure, and an enzyme displacement region. Such methods further comprise the use of an enzyme that translocates the polynucleotide through a nanopore against a voltage force when the enzyme activity blocking structure is removed. The enzyme blocking structure is reconstituted by movement of the enzyme. Also provided are methods for providing a polynucleotide comprising an abasic region, a region to be analyzed, a GQ fold, and an enzyme binding site, where such methods further comprise removing one enzyme molecule at the abasic region and allowing another enzyme molecule to bind at the enzyme binding site.

12 Claims, 5 Drawing Sheets

Specification includes a Sequence Listing.

NANOPORE SEQUENCING OF POLYNUCLEOTIDES WITH MULTIPLE PASSES

CROSS-REFERENCE TO RELATED APPLICATIONS

This application is a divisional of U.S. patent application Ser. No. 15/515,012, filed Mar. 28, 2017, which is a 371 application of PCT/US2015/052698, filed Sep. 28, 2015, which claims the benefit of U.S. Provisional Patent Application No. 62/056,963, filed Sep. 29, 2014, which applications are incorporated herein by reference in their entireties.

STATEMENT OF GOVERNMENTAL SUPPORT

This invention was made with Government support under Grant No. HG006321 and HG007827, awarded by the National Institutes of Health. The Government has certain rights in the invention.

BACKGROUND OF THE INVENTION

Field of the Invention

The present invention relates to the field of polynucleic acid sequencing and analysis, and, in particular to the field of polynucleic acid analysis using one or more nanopores through which the polynucleic acid is translocated.

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Nanopore sequencing is emerging as a means to low cost, high throughput DNA sequencing. Nanopore sequencing is based on the property of physically sensing the individual nucleotides (or physical changes in the environment of the nucleotides (that is, for example, an electric current)) within an individual polynucleotide (for example, DNA and RNA) as it traverses or translocates through a nanopore aperture. Nanopore devices are described in the literature, such as cited herein.

A nanopore system as described here can be used to sequence nucleic acid polymers using a number of previously described steps, such as by suspending a protein nanopore channel in a membrane separating two buffered salt solutions (typically 0.3M KCl, 25 mM HEPES pH 8.0) and applying a voltage across the membrane. When a nucleic acid polymer passes through the nanopore, it partially blocks the ionic current through the nanopore in a characteristic way unique to the sequence of the polymer. However, currently state of the art techniques only afford a single read of the captured molecule. The current state of the art is described, for example in US 20050053961, "Characterization of individual polymer molecules based on monomer-interface interactions," US 20060063171, "Methods and apparatus for characterizing polynucleotides," US 20070281329, "Characterization of individual polymer molecules based on monomer-interface interactions," US 20080102504, "Methods and apparatus for characterizing polynucleotides," and US 20110005918, "Compositions, devices, systems, and methods for using a nanopore," all of which are hereby incorporated by reference and constitute descriptions of various components and electronic controls for a nanopore sensor for use with the present invention. Furthermore, the various nanopores for use here are described, as are different enzymes used to modulate the translocation of the polymer through the nanopore.

Voltage control across the nanopore and membrane can be carried out as described, e.g. in Akeson et al. US 20140034517, "Compositions, Devices, Systems, and Methods for Using a Nanopore." As illustrated in FIG. 4 thereof, A DNA molecule with both doubled-stranded and single-stranded segments is captured in a nanoscale pore under an applied voltage (trans side positive) (Step a: of FIG. 4 the '517 publication). DNA of this nature can be generated by timed exonuclease digestion of restriction fragments from genomic DNA or from BAC clones etc. The nanopore is large enough to permit translocation of the ssDNA segment, but the double-stranded segment cannot translocate because its diameter is too large to fit through the narrowest part of the pore. The α-hemolysin pore is ideal for this and is therefore used to illustrate the technique. Strand capture and entry of the duplex segment into the pore vestibule can be confirmed based on current amplitude. Once this is achieved, the voltage is reduced under feedback control (Step b). At this point, the duplex terminus can be examined and identified by any of several techniques. For example, an earlier patent from this laboratory demonstrated that duplex termini can be identified based on DC current impedance alone. At the same time, the 5'-end of the ssDNA on the trans side of the channel is annealed to an agent (for example, a complementary oligonucleotide or streptavidin) that keeps the strand in the pore indefinitely. Control of the voltage can be facilitated by a finite state machine that controls and senses the biochemical state of the complex off single (or multiple) molecules associated with the biological nanopore. The finite state machine allows low latency control of the complex of molecules associated with the biological nanopore and at the same time can store information gathered for retrieval at another time.

As is known, nanopore sequencing does not require DNA amplification. It is further known that an MspA nanopore can be used to detect certain epigenetic markers. See, e.g. Proc Natl Acad Sci USA. 2013 Nov. 19; 110(47):18910-5, "Error rates for nanopore discrimination among cytosine, methylcytosine, and hydroxymethylcytosine along individual DNA strands."

There is currently a need for methods to obtain highly accurate polynucleic acid sequence information. Improved accuracy of a nanopore technique for sequencing polynucleic acids, including enhanced identification of epigenetic modifications of DNA, is desired.

BRIEF SUMMARY OF THE INVENTION

The following brief summary is not intended to include all features and aspects of the present invention, nor does it imply that the invention must include all features and aspects discussed in this summary.

Figure 3:
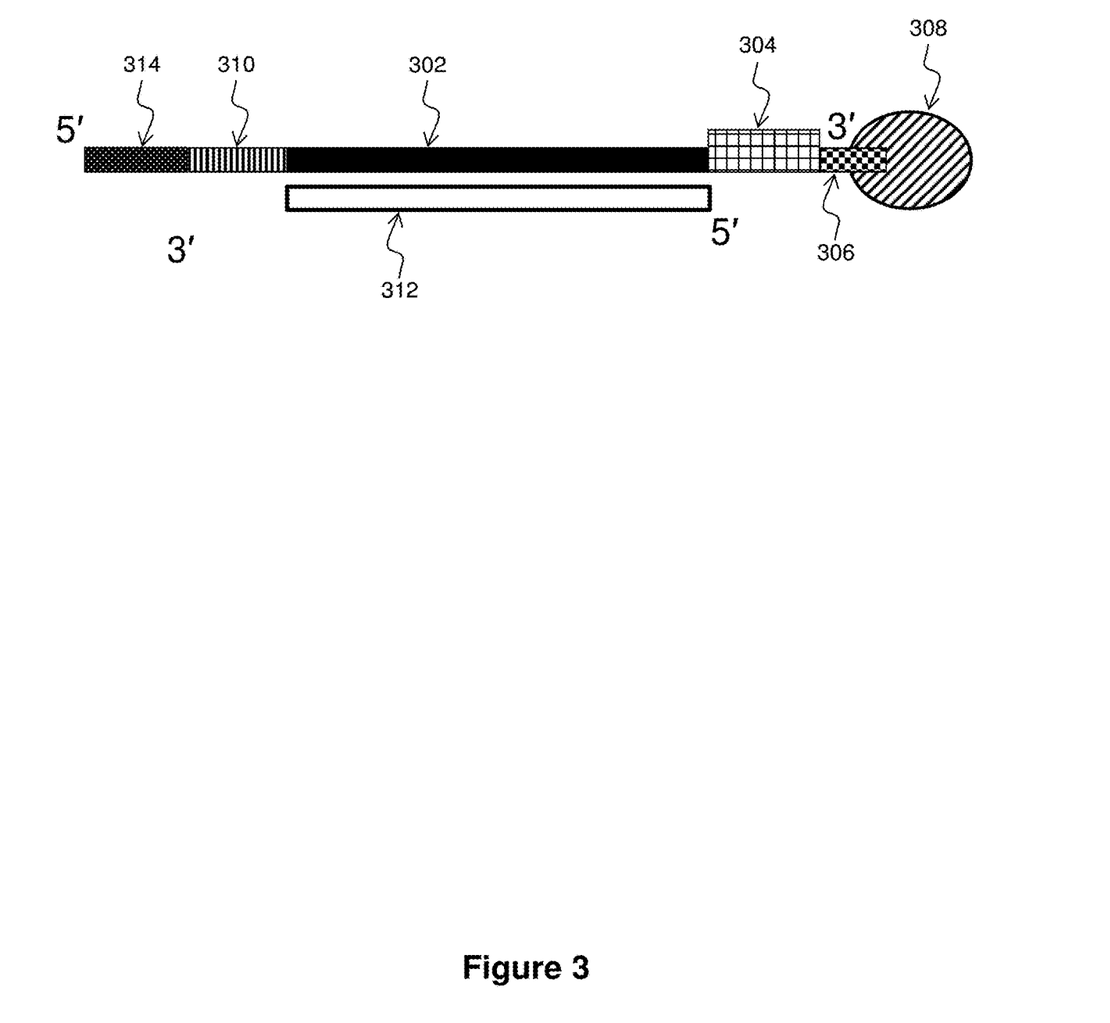
FIG. 3 is a schematic representation of a construct of a polymer for analysis, comprising a strand with an enzyme binding sequence, folded portion and an enzyme displacement portion.
Figure 4:
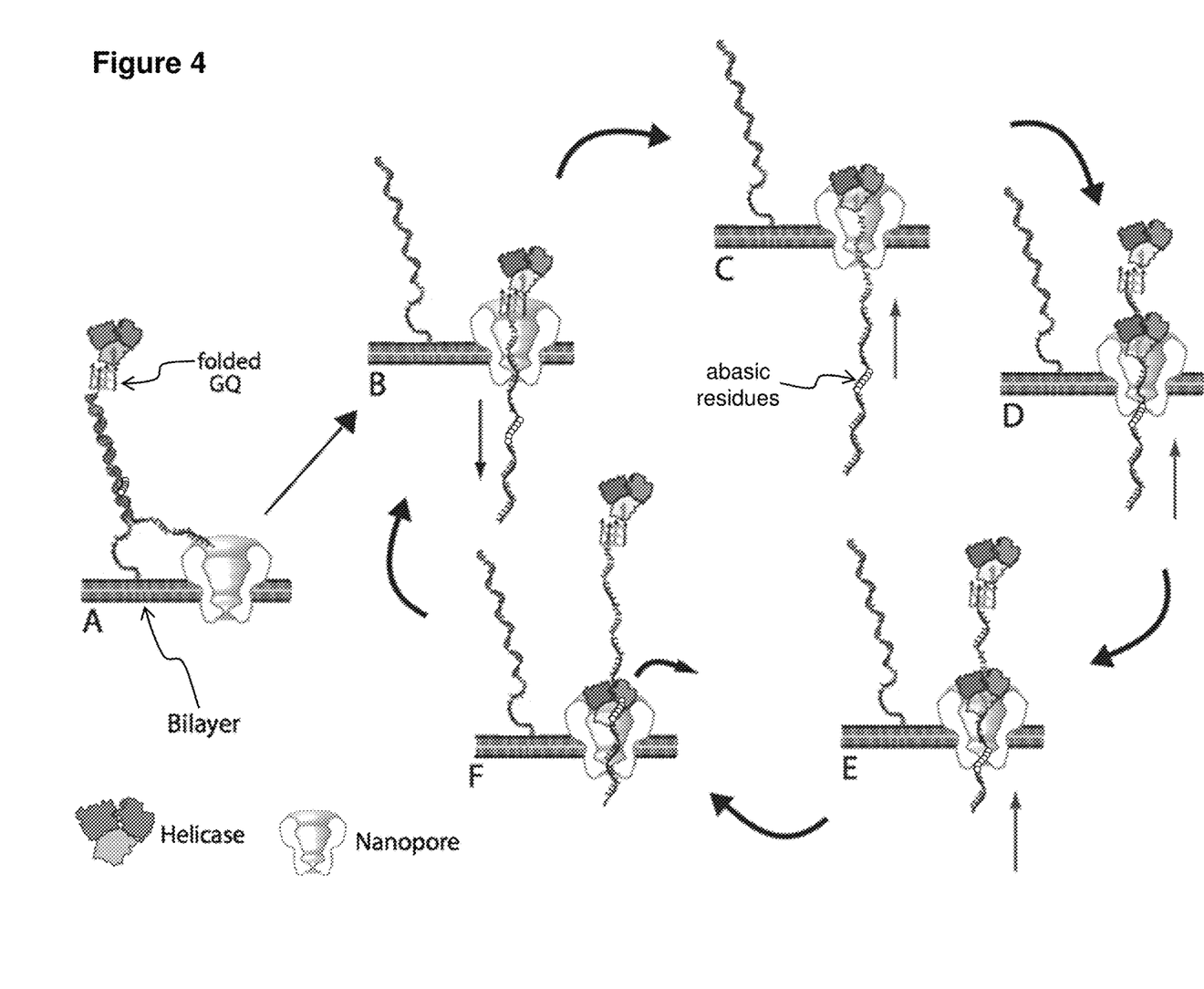
FIG. 4 is a schematic diagram illustrating an alternative embodiment of the scheme in FIG. 1, wherein one strand of the polynucleotide to be analyzed is anchored in the membrane (lipid bilayer) and the second strand passes through the nanopore in a reciprocating ("flossing") fashion as in the scheme of FIG. 1. Again, the straight arrows indicate the direction of the single strand through the pore. The darker arrows indicate the progress of the process form steps A though B to F and then back to B. The dotted arrow in step F shows the detachment of the enzyme from the strand, where the strand again moves in a trans direction through the nanopore.

The present invention comprises, in certain aspects, a polynucleotide construct useful in nanopore analysis, comprising a polynucleotide to be sequenced that has been ligated to specific sequences flanking the stand protein of interest, as shown, e.g. in FIG. 3. In particular, the construct comprises (a) a strand portion of interest, in said polynucleotide, to be analyzed in the nanopore; (b) a folded sequence in said polynucleotide, for blocking enzyme activity on the construct, located adjacent at a first end of the strand portion of interest; (c) an enzyme binding sequence in said polynucleotide, located such that the folded sequence is between it and the strand portion of interest and adjacent to the folded sequence, wherein a processive enzyme in the nanopore system can act on the construct; (d) an enzyme displacement sequence in said polynucleotide, located on an opposite side of the strand portion of interest, structured whereby an enzyme cannot bind to the enzyme displacement sequence when it encounters the enzyme displacement sequence; and (e) a single-stranded thread sequence in the polynucleotide at a terminal end of the construct, constructed to thread the polynucleotide into the nanopore, and located adjacent to the enzyme displacement sequence, such that the enzyme displacement sequence is between the thread sequence and the strand portion of interest.

In certain aspects, the present the polynucleotide construct comprises A partially single stranded portion, but further comprises a double-stranded portion in the strand sequence of interest. That is, the portion of the construct that is the strand portion of interest will be double stranded. This may be found in polynucleotides such as dsDNA obtained from various biological sources, such as genomic DNA and human genomic DNA. In certain aspects, the present construct comprises a single-stranded portion that comprises certain synthetic constructs here.

In certain aspects, the present construct comprises a folded sequence that is a G quadruplex. In certain aspects, the G quadruplex has a sequence that is one of SEQ ID NO: 1, 2, 3, or 4.

In certain aspects, the present construct further comprises an enzyme binding sequence comprises the sequence 5 dC. In certain aspects, this sequence is used with a helicase, and, for example, an Hel308 helicase.

In certain aspects, the present construct further comprises an enzyme displacement sequence that is an abasic series of nucleotide sugars. The enzyme displacement sequence causes the processive enzyme used on the construct to fall off the construct.

In certain aspects, the present construct comprises a strand portion of interest that is DNA or RNA obtained from a biological source.

In certain aspects, the present invention comprises a method for analyzing properties of a target portion polynucleotide using a nanopore in a membrane separating a cis fluid area from a trans fluid area, and a voltage source and current detector, comprising the steps of: (a) adding to the cis fluid side a polynucleotide to be analyzed, said polynucleotide having a target portion adapted to contain an enzyme binding site at one end, an enzyme blocking sequence adjacent to the enzyme binding site, and, at an opposite end of the target portion, an enzyme displacement region; (b) adding a processive enzyme to the fluid on the cis side and allowing a processive enzyme to bind to the enzyme binding site of the polynucleotide on the cis side; (c) drawing the polynucleotide through the nanopore to the trans side by a charge on the polynucleotide and thereby removing blocking in the blocking sequence on the cis side; (d) allowing the enzyme, bound to the enzyme binding site, to processively draw the polynucleotide from step (c) through the nanopore, from the trans side towards the cis side, while detecting current changes from nucleotides passing through the nanopore, said current changes being indicative of polynucleotide properties; (e) said enzyme being displaced by the displacement region when it reaches the displacement region by the processive drawing of step (d); (f) whereby displacement of the enzyme in step (e) causes voltage to again draw the polynucleotide through the nanopore, as in step (c), and an enzyme that has attached again to the polynucleotide on the cis side, processively draws the polynucleotide through the nanopore.

In certain aspects, the present method comprises detecting current charges occurs more than once on a single polynucleotide in a single or multiple nanopores. The current changes will occur in response to different base identities, and, further, base identities will be read more than once, as shown, e.g. in FIG. 2. In certain aspects, the present method comprises the use of a nanopore that is one of a carbon-formed nanopore, an alpha-hemolysin nanopore, and an MspA nanopore. In certain aspects, the present method comprises the use of a processive enzyme that is a helicase and wherein the enzyme binding site is specific for said helicase. In certain aspects, the present method is one wherein the helicase is an Hel308 helicase having at least 95% sequence identity to HELQ.

In certain aspects, the present inventive method comprises the use of an enzyme blocking sequence in a polynucleotide region that contains at least one hairpin turn. In certain aspects, the present method comprises a blocking sequence is a G-quadruplex.

In certain aspects, the present inventive method comprises an enzyme displacement region is a number of adjacent abasic nucleotide residues.

In certain aspects, the present invention comprises a method wherein the voltage polarity is not reversed during a given sequence analysis. In certain aspects, the present inventive method comprises detecting non-canonical bases. This is indicated by a current signal in the electronics described below. In certain aspects, the present method comprises analyzing a polynucleotide that is RNA, e.g. mRNA or rRNA. In certain aspects, the present inventive method comprises analyzing a polynucleotide in a nanopore-based device, characterized by modifying the polynucleotide to comprise, at one end region, an enzyme binding site adjacent to an enzyme activity blocking structure and, at a second end region, an enzyme displacement region, wherein the method further comprises the use of an enzyme that translocates the polynucleotide against a voltage force when the enzyme activity blocking structure is removed, and said enzyme blocking structure is reconstituted by movement of the enzyme.

In certain aspects, the present inventive method comprises a method for analyzing a polynucleotide comprising providing a polynucleotide comprising an abasic region at one end and a GQ fold at an opposite end. In certain aspects, the present inventive method comprises removing one enzyme molecule at the enzyme removal sequence and allowing another enzyme molecule to bind at the enzyme binding site.

It will be understood from the present text that the individual features described above may be combined in a variety of embodiment as described in the various figures and examples below.

DETAILED DESCRIPTION OF THE PREFERRED EMBODIMENT

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, the term "about" means plus or minus 5% of a stated numerical value.

A strand portion of interest refers a strand in a polynucleotide that is to be analyzed in a nanopore device. Suitable nanopore devices are known in the art, e.g. U.S. Pat. No. 6,015,714), U.S. Pat. Nos. 6,936,433, 7,189,503, 7,947,454, 8,679,747, etc. The strand may be analyzed to its primary base sequence, the presence in the sequence of modified bases, etc.

The term "folded sequence" refers to a region of a polynucleotide strand that contains bonds between bases in a single strand. An example, described in detail below, is a G-quaduplex. Depending on how the individual runs of guanine bases are arranged in a bimolecular or intramolecular quadruplex, a quadruplex can adopt one of a number of topologies with varying loop configuration. For other folded sequences, see Burge et al., "Quadruplex DNA: sequence, topology and structure," Nuc. Acids. Res. 34:5402-54125 (2006) and the discussion below.

An "enzyme binding sequence" is dependent on the enzyme used in the present system. A helicase used in the present example binds at a region distal to the folded sequence. As described below, the sequence 'NNNNN' denotes a loading site for the helicase that is experimentally determined based on the enzyme used. In the example, helicase Hel308Mbu use 5 dC residue.

The term "nanopore" is used in the conventional sense and will typically be a protein nanopore such as mSPa, α-hemolysin, etc. The nanopore will be inserted into a membrane and control electronics will be used to measure current and other features across the nanopore, as described in the patents referenced above. It is also understood that a nanopore that permits a sequential translocation of a single strand of a polynucleotide under voltage control can be fabricated our of an inert material such as carbon or silicon. A suitable nanopore used has dimensions such as found in alpha-hemolysin namely, a vestibule and a narrower (1.4-nm in diameter) part of the channel located at the base of the stem.

The term "nanopore analysis" is used to refer to an analytical method and device using a nanopore in a thin membrane and associated electronics to control and measure movement of a polynucleotide through the nanopore, preferably wherein the movement is modulated by an enzyme. For further details, see e.g. Olasagasti et al., "Compositions, devices, systems, for using a nanopore, U.S. Pat. No. 8,679, 747, describing devices and methods that can detect and control an individual polymer in a mixture is acted upon by another compound in a nanopore, used to determine rapidly (>50 Hz) the nucleotide base sequence of a polynucleotide under feedback control or using signals generated by the interactions between the polynucleotide and the nanopore.

The term "helicase" is used here to refer to a native or engineered enzyme or enzyme fragment that is capable of unwinding a double stranded nucleic acid enzymatically. For example, helicases are enzymes that are found in all organisms and in all processes that involve nucleic acid such as replication, recombination, repair, transcription, translation and RNA splicing. (See description in EP 2420579). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W.H. Freeman and Company (2nd ed. (1992)), include E. coli helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in HDA include RecQ helicase (Harmon and Kowalczykowski, J. Biol, Chem. 276: 232-243 (2001)), thermostable UvrD helicases from *T. tengcongensis* and *T. thermophilus* (Collins and McCarthy, Extremophiles. 7: 35-41. (2003)), thermostable DnaB helicase from *T. aquaticus* (Kaplan and Steitz, J. Biol. Chem. 274: 6889-6897 (1999)), and MCM helicase from archaeal and eukaryotic organisms (Grainge et al., Nucleic Acids Res. 31: 4888-4898(2003)). Helicase Hel308Mbu is described in WO 2014013260, "Modified Helicases." The helicase Hel308 is described in Richards et al., "Structure of the DNA Repair Helicase Hel308 Reveals DNA Binding and Autoinhibitory Domains," Feb. 22, 2008 The Journal of Biological Chemistry, 283, 5118-5126.

For purposes of identifying a suitable helicase for use with the present methods, one may obtain the sequence of HELQ, as (SEQ ID NO: 5)
DECGSRIRRRVSLPKRNRPSLGCIFGAPTAAELEPGDEGKEE

EEMVAENRRRKTAGVLPVEVQPLLLSDSPECLVLGGGDTNPDLLR

HMPTDRGVGDQPNDSEVDMFGDYDSFTENSFIAQVDDLEQKYMQ

LPEHKKHATDFATENLCSESIKNKLSITTIGNLTELQTDKHTENQSG

YEGVTIEPGADLLYDVPSSQAIYFENLQNSSNDLGDHSMKERDWK

SSSHNTVNEELPHNCIEQPQQNDESSSKVRTSSDMNRRKSIKDHLK

NAMTGNAKAQTPIFSRSKQLKDTLLSEEINVAKKTVESSSNDLGPF

YSLPSKVRDLYAQFKGIEKLYEWQHTCLTLNSVQERKNLIYSLPTS

GGKTLVAEILMLQELLCCRKDVLMILPYVAIVQEKISGLSSFGIELG

FFVEEYAGSKGRFPPTKRREKKSLYIATIEKGHSLVNSLIETGRIDSL

GLVVVDELHMIGEGSRGATLEMTLAKILYTSKTTQIIGMSATLNNV

EDLQKFLQAEYYTSQFRPVELKEYLKINDTIYEVDSKAENGMTFSR

LLNYKYSDTLKKMDPDHLVALVTEVIPNYSCLVFCPSKKNCENVA

EMICKFLSKEYLKHKEKEKCEVIKNLKNIGNGNLCPVLKRTIPFGV

AYHHSGLTSDERKLLEEAYSTGVLCLFTCTSTLAAGVNLPARRVIL

RAPYVAKEFLKRNQYKQMIGRAGRAGIDTIGESILILQEKDKQQVL

ELITKPLENCYSHLVQEFTKGIQTLFLSLIGLKIATNLDDIYHFMNG

TFFGVQQKVLLKEKSLWEITVESLRYLTEKGLLQKDTIYKSEEEVQ

YNFHITKLGRASFKGTIDLAYCDILYRDLKKGLEGLVLESLLHLIYL

TTPYDLVSQCNPDWMIYFRQFSQLSPAEQNVAAILGVSESFIGKKA

SGQAIGKKVDKNVVNRLYLSFVLYTLLKETNIWTVSEKFNMPRGY

IQNLLTGTASFSSCVLHFCEELEEFWVYRALLVELTKKLTYCVKAE

LIPLMEVTGVLEGRAKQLYSAGYKSLMHLANANPEVLVRTIDHLS

RRQAKQIVSSAKMLLHEKAEALQEEVEELLRLPSDFPGAVASTD

KA.

The above helicase sequence is merely one of a number of helicase sequences that can be used. The exact sequence used may also be varied by a number of amino acid alterations. For example, one may use a helicase having sequence identity to the above sequence of 100%, 95%, 90%, 85%, 80%, etc.

However, other equivalent enzymes such as DNA repair enzymes, recombinases, etc. may be substituted for the helicase.

The term "single-stranded thread sequence" refers to the property of the present nanopore to accept only a single strand of a partially duplex polynucleotide.

The term "processive enzyme" has the conventional meaning of an enzyme that moves relative to a polynucleotide before dissociating from the polynucleotide. A processive helicase is described, e.g. in Lahue et al., "*Escherichia coli* DNA helicase I catalyzes a Unidirectional and Highly Processive Unwinding Reaction," J. Biol. Chem. 263:3208-3215 (1987).

Sequence Identity

The term "substantial sequence identity" in the context of a polypeptide enzyme indicates that a polypeptide comprises a sequence with at least 95% sequence identity to the reference sequence over a specified comparison window, which in this case is either the entire peptide, a molecular scaffold portion, or a binding loop portion (~9-11 residues). Preferably, optimal alignment is conducted using the homology alignment algorithm of Needleman and Wunsch (1970) J. Mol. Biol., 48:443 453. An indication that two peptide sequences are substantially identical is that one peptide is immunologically reactive with antibodies raised against the second peptide. Another indication for present purposes, that a sequence is substantially identical to a specific sequence explicitly exemplified is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified, e.g., by the PAM 250 scoring matrix. Peptides that are "substantially similar" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (helixweb.nih.gov/multialign/). Three-dimensional tools may also be used for sequence comparison.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Overview

The present invention comprises a method for using certain adapters to a single-stranded nucleic acid polymer (for example, DNA or RNA) for use with nanopore sequencing. This invention allows for the base-by-base control of the polymer through a nanopore using an enzyme bound to the polymer, such as helicase enzyme as exemplified here. The polymer is ligated to special sequences added at either end of the polymer that allow for the polymer to be reread (passed multiple times) through the nanopore under enzymatic control. The benefit of this strategy is to increase accuracy of DNA or RNA nanopore sequencing. This strategy increases accuracy in nanopore sequencing devices both for DNA modifications as well as typical base calling. It also has the advantage of removing stochastic undesired enzyme behavior by comparing reads of the same molecule. However, this strategy is fundamentally limited by the processivity of the enzyme (how many bases can it pull through the nanopore before dissociating at a site other than the 5' linker region).

The invention as exemplified here employs DNA adapters that allow for multiple passes of a single nucleic acid polymer molecule through a nanopore under enzymatic control. This allows for multiple reads of the same molecule during sequencing of the polymer. In our current experiments we use exclusively DNA; however, this strategy could be expanded to RNA sequencing. The principal of the method involves attaching two engineered DNA adapters to either end of a nucleic acid polymer to be interrogated. Attachment of the adapters can be accomplished using standard nucleic acid ligation procedures. The adapters can also be directly incorporated into the sequence of synthetic DNA/RNA. This method involves using a helicase enzyme to control the nucleic acid polymer through the nanopore. These enzymes have an innate polarity and travel 3' to 5' or 5' to 3', and this method can be implemented with either polarity enzyme. Most helicases translocate along one strand of the duplex while displacing the complementary strand (of either DNA or RNA). Thus, helicases have directionality. They move along nucleic acids in either the 3'-->5' or 5'-->3' direction. See, e.g. Shin et al. "DNA unwinding assay using streptavidin-bound oligonucleotides," BMC Mol Biol. 2006; 7: 43. Published online Nov. 28, 2006. For simplicity, we will assume an enzyme that has 3' to 5' directionality.

The 3' adapter (ref. 304 in FIG. 3) contains a sequence that folds into a secondary structure that inhibits the enzyme from translocating on the strand. Our experiments use a sequence that folds into an intramolecular G-quadruplex (GQ), and we have used the following sequences:

| Name | Sequence |
|---|---|
| Thrombin Binding Aptamer | 5' . . . GGTTGGTGTGGTTGGNNNNN (SEQ ID NO: 1) |
| c-Myc | 5' . . . GGGTGGGGAGGGTGGGNNNNN (SEQ ID NO: 2) |
| Telomere Repeat | 5' . . . GGGTTAGGGTTAGGGTTAGGGNNNNN (SEQ ID NO: 3) |
| 121 | 5' . . . GGGTGGGTTGGGTGGGNNNNN (SEQ ID NO: 4) |

In these adapter strands, the sequence to be interrogated (see 302 in FIG. 3) is located 3' to the GQ sequence (see 304 in FIG. 3), and the 'NNNNN' denotes a loading site for the helicase that is experimentally determined based on the enzyme used. Our experiments with Hel308Mbu use 5 dC residues as the enzyme loading site. When the strand is captured in the nanopore the force from the applied voltage unfolds the intramolecular GQ yielding single-stranded DNA and allowing the enzyme to translocate and ratchet the DNA against the voltage in discernable steps. Once the enzyme translocates through the GQ sequence, the GQ spontaneously refolds inhibiting additional enzymes from tracking on the strand.

The 5' adapter contains a block of abasic residues proximal to the end of the strand. These are regions of DNA that do not contain bases but are linked through phosphodiester backbone, or other covalent chemical linkage. The enzyme used must not be able to translocate through this region and as a result dissociates into solution while the strand remains captured in the nanopore. At this point, the voltage pulls the strand to the 3' GQ, which is unfolded and the read restarts. Initial experiments use d-spacers (abasic residues), however any linker that does not allow for the enzyme to translocate will work for this purpose, such as alkane or PEG linkers.

By rereading the same DNA molecule multiple times, we expect to be able to increase accuracy in detecting modifications (such as cytosine modifications, or non-canonical bases in RNA). Rereading also alleviates stochastic enzyme errors such as inserts and deletions because they will likely not be present in the same place of the sequence in two different reads.

The present method provides a more accurate analysis of the nucleotides in a polynucleotide. Accordingly, it can be used to detect chemical modifications of bases beyond the typical discrimination of A, T/U, G and C. In particular, it can be used to detect epigenetic chemical modification of polynucleotides.

Known epigenetic modifications of DNA include 5-methylcytosine, 5-hydroxymethylcytosine, 5-formylcytosine, and 5-carboxycytosine. Epigenetic modifications such as cytosine methylation, have been implicated in development and disease. Epigenetic modifications of DNA are known to help regulate gene transcription in biological cells, and accurate identification of epigenetic modifications of DNA is expected to shed light on a wide array of biological processes.

A polynucleotide sequence is generally determined from a statistical average of data in nanopore sequencing. Data obtained from multiple passages of the same molecule through a nanopore would be expected to improve the accuracy of sequence determination, including the proper identification of epigenetic modifications.

Figure 1:
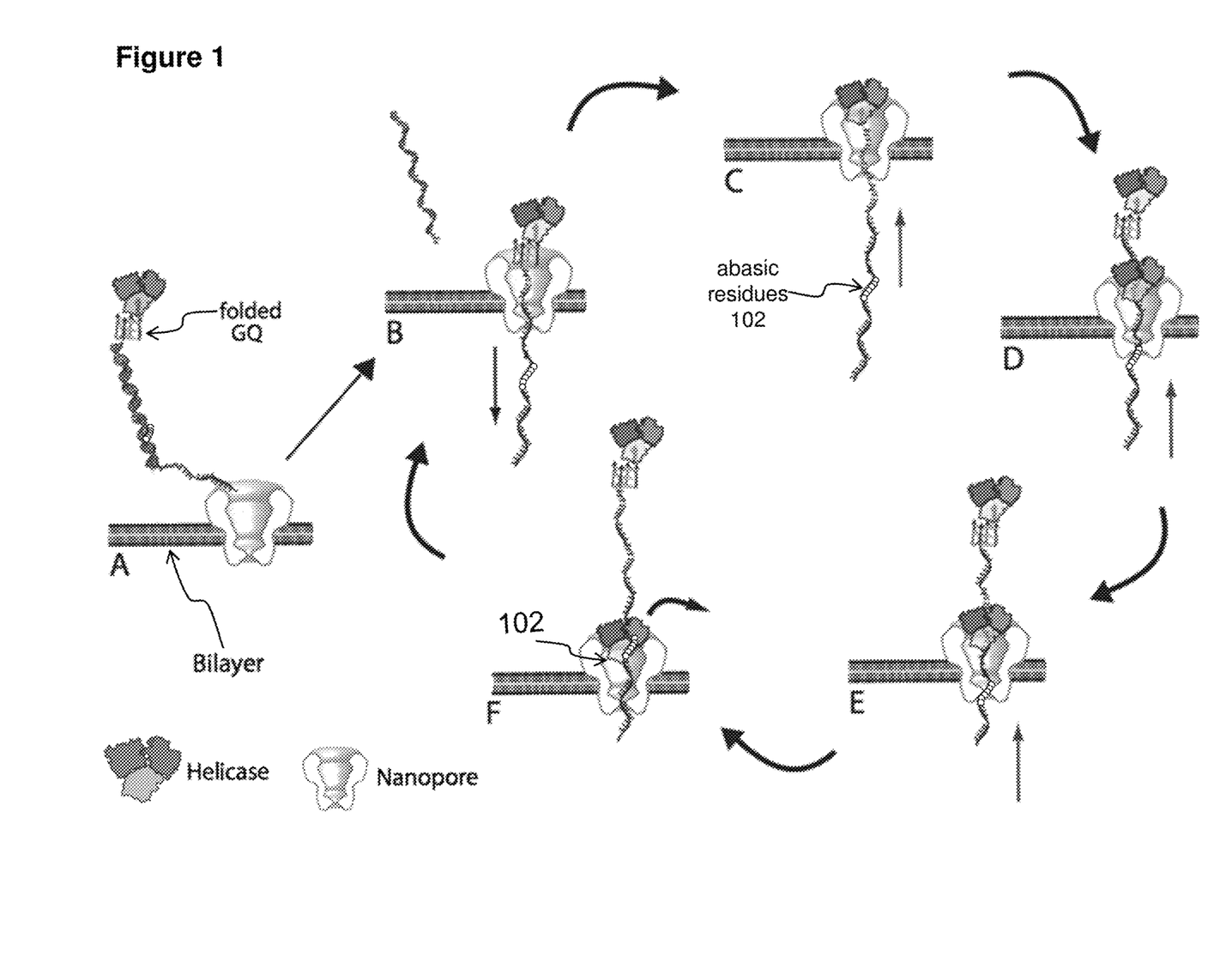
FIG. 1 is a schematic diagram illustrating a method of the present invention whereby a nucleic acid polymer sequenced using a nanopore is read multiple times. By convention, the initial side of the polymer is termed the cis side. The strand moves from A to B partially through the nanopore to the trans side, i.e., in the downward arrow.

FIG. 1 shows an overview of the process by which rereading of a polynucleotide takes place in a method of the present invention. The figure indicates sequential steps A) through F) and return of the sequence from F) to B) again. The sequence is: Step A) The strand, annealed to its complement, is captured by the nanopore. Step B) The voltage removes the complementary strand and positions the folded GQ between the helicase and the pore. The arrow shows the direction of voltage-mediated movement of the construct. Step C) The electric potential acting on the strand from the cis side to the trans side unfolds the GQ on the 3' adapter allowing the helicase to ratchet DNA through the nanopore sensor. The arrow shows the movement caused by the enzyme. Step D) The enzyme ratchets the DNA against the voltage, allowing sequencing of the strand as it passes through the nanopore, and the GQ refolds behind the helicase. Again, the arrow shows enzyme-caused movement. Step E) On the 5' adapter, a region of abasic residues (102, within the pore) do not allow for helicase/DNA binding and the enzyme dissociates back into solution. Again, the arrow shows enzyme caused movement. Step F). At this point, the electric potential pulls the strand to the starting position at the GQ and the read starts over. The curved arrow at F indicates that at this point the helicase that encounters the abasic region and, as a result, falls off of the strand. Voltage is switched to pull the complex back through the pore, as shown in the downward arrow in B.

Briefly, FIG. 3 illustrates a strand portion of interest 302 (i.e. to be sequenced); 304 showing a folded sequence (e.g. GQ) adjacent to the strand of interest; 306 showing an enzyme binding sequence between the folded sequence 304 and the enzyme binding site 306; 310 on the other side of the folded sequence, showing an enzyme displacement sequence; and adjacent to that is a thread threading sequence 314.

As shown in FIG. 3, the present invention comprises a construct of a polymer for analysis that is, for example, a double stranded polynucleotide, e.g. DNA, which may be genomic DNA, dsRNA, an RNA-DNA hybrid, or the like. A strand portion of the construct to be analyzed 302, is typically in double stranded form, being base-pair hydrogen bonded to a complement strand 312. Strand 312 is typically removed or stripped off by the nanopore, which will only accept a single stranded polynucleotide through its narrowed portion, as the strand is forced through the nanopore by the applied voltage. The first strand portion 302, to be analyzed, or sequenced, is shown as accepting an enzyme, e.g. helicase 308 at the 3' end distal to the strand to be sequenced.

The strand portion to be analyzed 302 is modified to contain an abasic stretch (310) in the 5' region, with a single stranded portion (314) to be threaded into the nanopore. The strand to be analyzed further contains at the 3' end a folded portion 304, such as a GQ region. The GQ region is further described in Shin & Gu, "Single-molecule investigation of G-quadruplex using a nanopore sensor," Methods. 2012 May; 57(1):40-6. Epub 2012 Apr. 2. The G-quadruplex, for simplicity, may be regarded as nucleic acid sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex.

Located 3' of the folded portion 304 is a loading sequence 306 that is designed to allow the DNA modifying enzyme, preferably a helicase 308, to initiate activity on the stand to be analyzed, 302. As described above, if the folded portion 304 is in place, the enzyme will bind to the strand, but will not move forward past the folded portion, when it is folded.

For a 5'→3' helicase, the order of the construct is reversed, i.e. 306, then 304, then 302, then 310, then 314, from left to right in the schematic of FIG. 3.

In summary, the construct has the following arrangement from end one to end two: abasic section, sequencing section, folded section, then enzyme loading section. End one may be either a 3' end or a 5' end. The terms a 3' end and a 5' end refer to conventional directionality used in molecular biology. The chemical convention of naming carbon atoms in the nucleotide sugar-ring numerically gives rise to a 5'-end and a 3'-end. This is illustrated below:

EXAMPLE

As a single molecule technique, nanopore sequencing reads individual DNA strands and has the opportunity to characterize subpopulations within samples that would be averaged away by conventional ensemble techniques. In the present study we have engineered a nanopore system based on Hel308 helicase-controlled DNA translocation through an MspA protein nanopore that can reread a single molecule of DNA multiple times. This design uses the single-strand DNA translocation ability of Hel308 to pull DNA against an applied voltage through the MspA pore. At the end of each read the enzyme dissociates into solution but the molecule is retained in the pore. Additional Hel308 that are staged at the beginning of the strand reread the molecule. This technique affords similar advantages of averaging reads of a population of molecules in terms of accuracy but characterizes one molecule of DNA. We have applied our technology to increasing the accuracy of calling methyl and hydroxymethyl cytosine modification at CpG dinucleotides using machine-learning methods. We compared the accuracy of a single read to multiple reads and have shown that rereading increases the accuracy of a correct call between the three cytosine variants. In order to increase speed and minimize bias of data analysis we have implemented a computer-based system for event picking and segmentation of current traces. We have implemented a machine learning system that removes undesired stochastic enzyme behavior such as back slipping.

Figure 2:
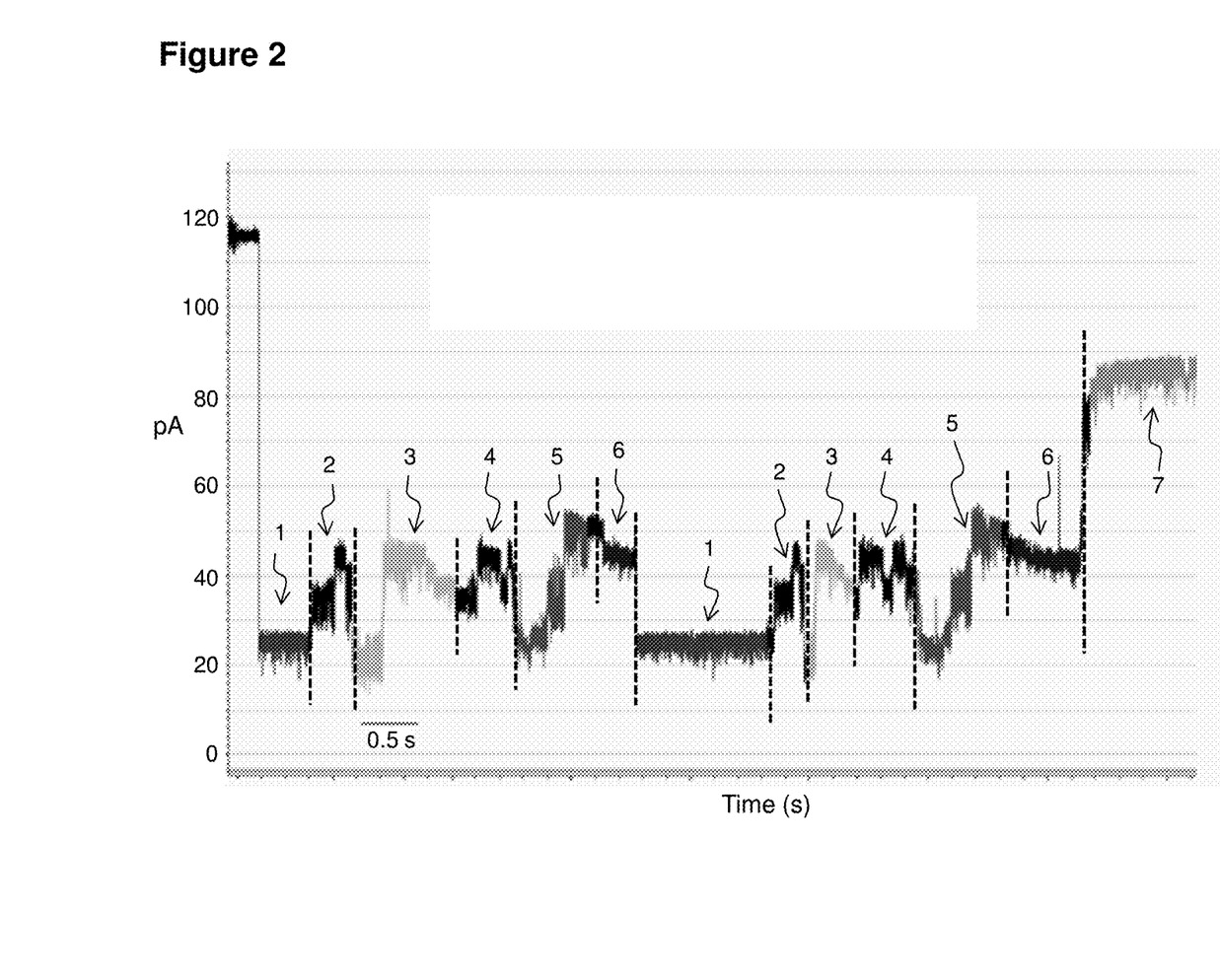
FIG. 2 is a data plot showing a current trace obtained according to the present invention by nanopore sequencing of a DNA oligonucleotide.

Real-time data obtained by the present method is shown in FIG. 2. The DNA sequence responsible for the observable current is shown as follows:

| Segment 7 | Segment 6 | Segment 5 | Segment 4 |
|---|---|---|---|
| XXXXXXX (X7) (abasic) | $C_7$ | CATTTTCA | TC |

| Segment 3 | Segment 2 | Segment 1 | (SEQ ID NO: 8) |
|---|---|---|---|
| ATCCCGGT | CAT | $T_9$ | |

The segments 1-7 correspond to the indicated sequences, with the abasic segment 7 at the right side of the trace. The sequence of the oligo used to produce this data is:
5'TTTTTTTTTTTTTTTTTTTTTTTTTTTTTTCCCCC-CCCCCCCXXXXXXXXX XXCCCCCCCCATTTT-CATCATCChmCGGTCAT-TTTTTTTTTTTTTTTTTGGTTGGT GTGGTTGGCCCCC (SEQ ID NO: 6), where X indicates abasic residues and hmC indicates a hydroxymethylcytosine base.

The parts of the current trace resulting from passage of the different sections of the sequence through the nanopore are labeled with the corresponding numbers. In this example, it can be seen that the oligonucleotide sequence is "re-read", passing through the nanopore twice: it passes through once in the order 7, 6, 5, 4, 3, 2, and then it passes through a second time in the same order.

Figure 5:
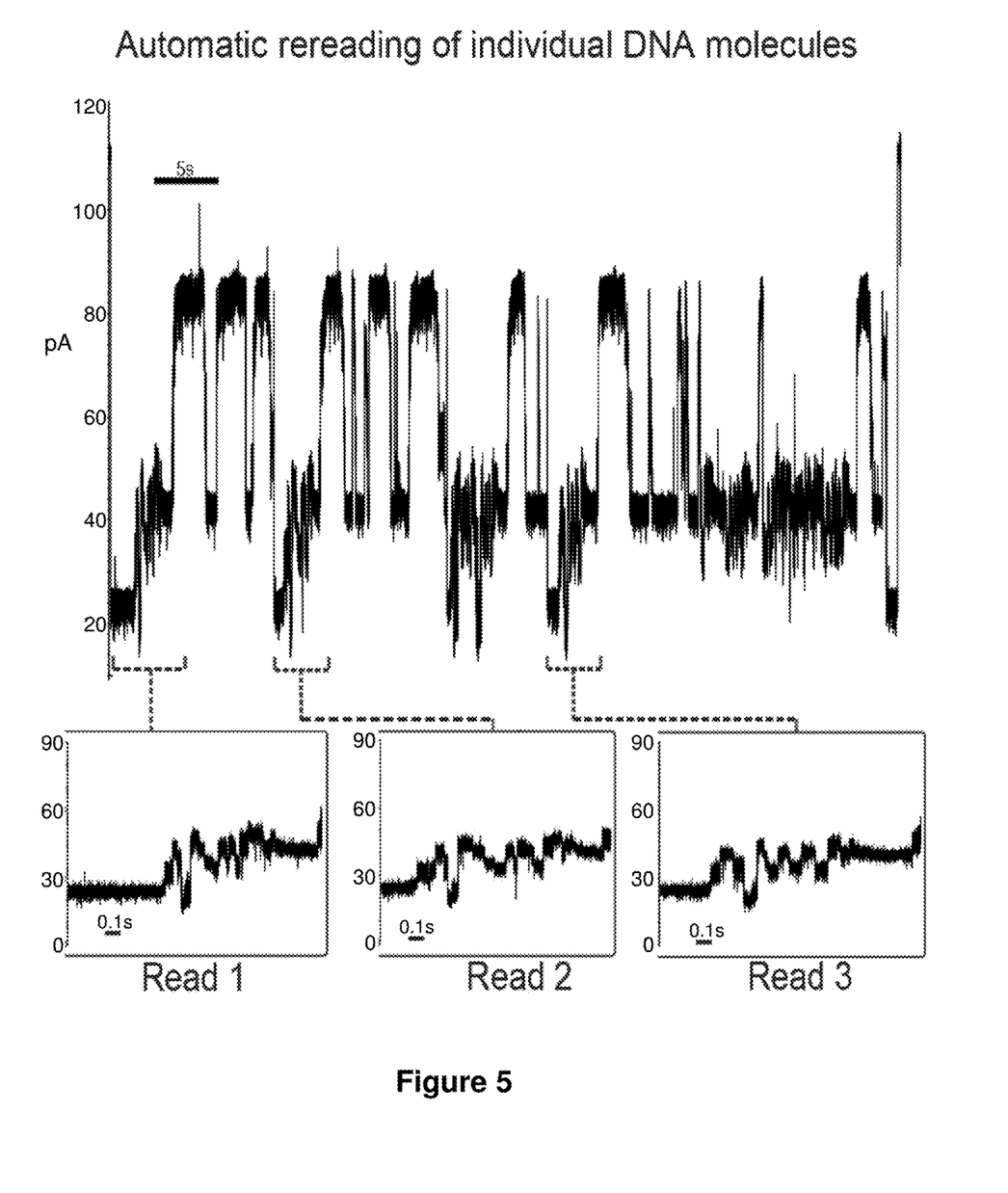
FIG. 5 is a data plot showing current trace of automatic rereading of a molecule of DNA with 3 individual reads expanded.

Similarly, FIG. 5 shows a real time data plot of a long capture event with three reads highlighted. The sequence of the oligo used in this trace is:

5'TTTTTTTTTTTTTTTTTTTTTTTTTTTCCCC-CCCCCCCCXXXXXXXXXX XXCCCCCCCCATAAT-CATCATCCmCGGTCATTTTTTTTTTTTTTTTT-TTTGGTTGGT GTGGTTGGCCCCC (SEQ ID NO: 7), where X indicates abasic residues and mC indicates 5-methylcytosine.

CONCLUSION

The above specific description is meant to exemplify and illustrate the method and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material to which is referred.

What is claimed is:

1. A method for analyzing properties of a target portion of a polynucleotide using a nanopore in a membrane separating a cis fluid area from a trans fluid area, and a voltage source and current detector, comprising:
   (a) adding to the cis fluid side a polynucleotide comprising a target portion to be analyzed, said polynucleotide comprising in order: an enzyme binding site, an enzyme blocking sequence, the target portion, an enzyme displacement region and a threading sequence;
   (b) adding a processive enzyme to the fluid on the cis side and allowing the processive enzyme to bind to the enzyme binding site of the polynucleotide on the cis side;
   (c) drawing the polynucleotide, beginning with the threading sequence, through the nanopore to the trans side by a charge on the polynucleotide and thereby removing blocking by the enzyme blocking sequence on the cis side;
   (d) allowing the processive enzyme, bound to the enzyme binding site, to processively draw the polynucleotide from step (c) through the nanopore, from the trans side towards the cis side, while detecting current changes from nucleotides passing through the nanopore, said current changes being indicative of polynucleotide properties;
   (e) said processive enzyme being displaced by the displacement region when it reaches the displacement region by the processive drawing of step (d); and
   (f) whereby displacement of the processive enzyme in step (e) causes voltage to again draw the polynucleotide through the nanopore, as in step (c), and a processive enzyme that has attached again to the polynucleotide on the cis side, processively draws the polynucleotide through the nanopore.

2. The method of claim 1, wherein said detecting current changes occurs more than once on a single polynucleotide in a single or multiple nanopores.

3. The method of claim 1, wherein said nanopore is one of carbon, alpha-hemolysin, and MspA.

4. The method of claim 1, wherein the processive enzyme is a helicase and the enzyme binding site is specific for said helicase.

5. The method of claim 4, wherein the helicase is an Hel308 helicase having at least 95% sequence identity to HELQ.

6. The method of claim 1, wherein the enzyme blocking sequence is a polynucleotide region containing at least one hairpin turn.

7. The method of claim 6, wherein the enzyme blocking sequence is a G-quadruplex.

8. The method of claim 1, wherein enzyme displacement region is a number of adjacent abasic nucleotide residues.

9. The method of claim 1, wherein the analyzing comprises detecting non-canonical bases.

10. The method of claim 1, wherein the polynucleotide is RNA.

11. A method for nanopore-based analysis of a polynucleotide, comprising by modifying the polynucleotide to comprise, at one end region, an enzyme binding site adjacent to an enzyme activity blocking structure and, at a second end region, an enzyme displacement region, wherein the method further comprises the use of an enzyme that translocates the polynucleotide through a nanopore against a voltage force when the enzyme activity blocking structure is removed, and said enzyme blocking structure is reconstituted by movement of the enzyme.

12. A method comprising:
providing a polynucleotide comprising in order: an abasic region, a region to be analyzed, a GQ fold, and an enzyme binding site; and
removing one enzyme molecule at the abasic region and allowing another enzyme molecule to bind at the enzyme binding site.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (16)..(20)
<223> OTHER INFORMATION: n = a, c, g, or t/u

<400> SEQUENCE: 1
ggttggtgtg gttggnnnnn                                                    20

<210> SEQ ID NO 2
<211> LENGTH: 21
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (17)..(21)
<223> OTHER INFORMATION: n = a, c, g, or t/u

<400> SEQUENCE: 2
gggtggggag ggtgggnnnn n                                                  21

<210> SEQ ID NO 3
<211> LENGTH: 26
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (22)..(26)
<223> OTHER INFORMATION: n = a, c, g, or t/u

<400> SEQUENCE: 3
gggttagggt tagggttagg gnnnnn                                             26

<210> SEQ ID NO 4
<211> LENGTH: 21
<212> TYPE: DNA
<213> ORGANISM: Artificial
<220> FEATURE:
<223> OTHER INFORMATION: Synthetically prepared oligonucleotide sequence
<220> FEATURE:
```

<220> NAME/KEY: misc_feature
<222> LOCATION: (17)..(21)
<223> OTHER INFORMATION: n = a, c, g, or t/u

<400> SEQUENCE: 4
gggtgggttg ggtgggnnnn n                                              21

<210> SEQ ID NO 5
<211> LENGTH: 1100
<212> TYPE: PRT
<213> ORGANISM: Homo sapiens

<400> SEQUENCE: 5

```
Asp Glu Cys Gly Ser Arg Ile Arg Arg Val Ser Leu Pro Lys Arg
1               5                   10                  15

Asn Arg Pro Ser Leu Gly Cys Ile Phe Gly Ala Pro Thr Ala Ala Glu
            20                  25                  30

Leu Glu Pro Gly Asp Glu Gly Lys Glu Glu Glu Met Val Ala Glu
        35                  40                  45

Asn Arg Arg Arg Lys Thr Ala Gly Val Leu Pro Val Glu Val Gln Pro
    50                  55                  60

Leu Leu Leu Ser Asp Ser Pro Glu Cys Leu Val Leu Gly Gly Gly Asp
65                  70                  75                  80

Thr Asn Pro Asp Leu Leu Arg His Met Pro Thr Asp Arg Gly Val Gly
                85                  90                  95

Asp Gln Pro Asn Asp Ser Glu Val Asp Met Phe Gly Asp Tyr Asp Ser
            100                 105                 110

Phe Thr Glu Asn Ser Phe Ile Ala Gln Val Asp Asp Leu Glu Gln Lys
        115                 120                 125

Tyr Met Gln Leu Pro Glu His Lys Lys His Ala Thr Asp Phe Ala Thr
    130                 135                 140

Glu Asn Leu Cys Ser Glu Ser Ile Lys Asn Lys Leu Ser Ile Thr Thr
145                 150                 155                 160

Ile Gly Asn Leu Thr Glu Leu Gln Thr Asp Lys His Thr Glu Asn Gln
                165                 170                 175

Ser Gly Tyr Glu Gly Val Thr Ile Glu Pro Gly Ala Asp Leu Leu Tyr
            180                 185                 190

Asp Val Pro Ser Ser Gln Ala Ile Tyr Phe Glu Asn Leu Gln Asn Ser
        195                 200                 205

Ser Asn Asp Leu Gly Asp His Ser Met Lys Glu Arg Asp Trp Lys Ser
    210                 215                 220

Ser Ser His Asn Thr Val Asn Glu Glu Leu Pro His Asn Cys Ile Glu
225                 230                 235                 240

Gln Pro Gln Gln Asn Asp Glu Ser Ser Lys Val Arg Thr Ser Ser
                245                 250                 255

Asp Met Asn Arg Arg Lys Ser Ile Lys Asp His Leu Lys Asn Ala Met
            260                 265                 270

Thr Gly Asn Ala Lys Ala Gln Thr Pro Ile Phe Ser Arg Ser Lys Gln
        275                 280                 285

Leu Lys Asp Thr Leu Leu Ser Glu Glu Ile Asn Val Ala Lys Lys Thr
    290                 295                 300

Val Glu Ser Ser Ser Asn Asp Leu Gly Pro Phe Tyr Ser Leu Pro Ser
305                 310                 315                 320

Lys Val Arg Asp Leu Tyr Ala Gln Phe Lys Gly Ile Glu Lys Leu Tyr
                325                 330                 335
```

-continued

```
Glu Trp Gln His Thr Cys Leu Thr Leu Asn Ser Val Gln Glu Arg Lys
                340                 345                 350

Asn Leu Ile Tyr Ser Leu Pro Thr Ser Gly Gly Lys Thr Leu Val Ala
            355                 360                 365

Glu Ile Leu Met Leu Gln Glu Leu Leu Cys Cys Arg Lys Asp Val Leu
        370                 375                 380

Met Ile Leu Pro Tyr Val Ala Ile Val Gln Glu Lys Ile Ser Gly Leu
385                 390                 395                 400

Ser Ser Phe Gly Ile Glu Leu Gly Phe Phe Val Glu Glu Tyr Ala Gly
                405                 410                 415

Ser Lys Gly Arg Phe Pro Pro Thr Lys Arg Arg Glu Lys Lys Ser Leu
            420                 425                 430

Tyr Ile Ala Thr Ile Glu Lys Gly His Ser Leu Val Asn Ser Leu Ile
        435                 440                 445

Glu Thr Gly Arg Ile Asp Ser Leu Gly Leu Val Val Asp Glu Leu
    450                 455                 460

His Met Ile Gly Glu Gly Ser Arg Gly Ala Thr Leu Glu Met Thr Leu
465                 470                 475                 480

Ala Lys Ile Leu Tyr Thr Ser Lys Thr Thr Gln Ile Ile Gly Met Ser
                485                 490                 495

Ala Thr Leu Asn Asn Val Glu Asp Leu Gln Lys Phe Leu Gln Ala Glu
            500                 505                 510

Tyr Tyr Thr Ser Gln Phe Arg Pro Val Glu Leu Lys Glu Tyr Leu Lys
        515                 520                 525

Ile Asn Asp Thr Ile Tyr Glu Val Asp Ser Lys Ala Glu Asn Gly Met
530                 535                 540

Thr Phe Ser Arg Leu Leu Asn Tyr Lys Tyr Ser Asp Thr Leu Lys Lys
545                 550                 555                 560

Met Asp Pro Asp His Leu Val Ala Leu Val Thr Glu Val Ile Pro Asn
                565                 570                 575

Tyr Ser Cys Leu Val Phe Cys Pro Ser Lys Lys Asn Cys Glu Asn Val
            580                 585                 590

Ala Glu Met Ile Cys Lys Phe Leu Ser Lys Glu Tyr Leu Lys His Lys
        595                 600                 605

Glu Lys Glu Lys Cys Glu Val Ile Lys Asn Leu Lys Asn Ile Gly Asn
    610                 615                 620

Gly Asn Leu Cys Pro Val Leu Lys Arg Thr Ile Pro Phe Gly Val Ala
625                 630                 635                 640

Tyr His His Ser Gly Leu Thr Ser Asp Glu Arg Lys Leu Leu Glu Glu
                645                 650                 655

Ala Tyr Ser Thr Gly Val Leu Cys Leu Phe Thr Cys Thr Ser Thr Leu
            660                 665                 670

Ala Ala Gly Val Asn Leu Pro Ala Arg Arg Val Ile Leu Arg Ala Pro
        675                 680                 685

Tyr Val Ala Lys Glu Phe Leu Lys Arg Asn Gln Tyr Lys Gln Met Ile
    690                 695                 700

Gly Arg Ala Gly Arg Ala Gly Ile Asp Thr Ile Gly Glu Ser Ile Leu
705                 710                 715                 720

Ile Leu Gln Glu Lys Asp Lys Gln Gln Val Leu Glu Leu Ile Thr Lys
                725                 730                 735

Pro Leu Glu Asn Cys Tyr Ser His Leu Val Gln Glu Phe Thr Lys Gly
            740                 745                 750

Ile Gln Thr Leu Phe Leu Ser Leu Ile Gly Leu Lys Ile Ala Thr Asn
```

```
                          755                 760                 765
Leu Asp Asp Ile Tyr His Phe Met Asn Gly Thr Phe Phe Gly Val Gln
770                 775                 780

Gln Lys Val Leu Leu Lys Glu Lys Ser Leu Trp Glu Ile Thr Val Glu
785                 790                 795                 800

Ser Leu Arg Tyr Leu Thr Glu Lys Gly Leu Gln Lys Asp Thr Ile
                805                 810                 815

Tyr Lys Ser Glu Glu Glu Val Gln Tyr Asn Phe His Ile Thr Lys Leu
                820                 825                 830

Gly Arg Ala Ser Phe Lys Gly Thr Ile Asp Leu Ala Tyr Cys Asp Ile
                835                 840                 845

Leu Tyr Arg Asp Leu Lys Lys Gly Leu Glu Gly Leu Val Leu Glu Ser
850                 855                 860

Leu Leu His Leu Ile Tyr Leu Thr Thr Pro Tyr Asp Leu Val Ser Gln
865                 870                 875                 880

Cys Asn Pro Asp Trp Met Ile Tyr Phe Arg Gln Phe Ser Gln Leu Ser
                885                 890                 895

Pro Ala Glu Gln Asn Val Ala Ala Ile Leu Gly Val Ser Glu Ser Phe
                900                 905                 910

Ile Gly Lys Lys Ala Ser Gly Gln Ala Ile Gly Lys Lys Val Asp Lys
                915                 920                 925

Asn Val Asn Arg Leu Tyr Leu Ser Phe Val Leu Tyr Thr Leu Leu
930                 935                 940

Lys Glu Thr Asn Ile Trp Thr Val Ser Glu Lys Phe Asn Met Pro Arg
945                 950                 955                 960

Gly Tyr Ile Gln Asn Leu Leu Thr Gly Thr Ala Ser Phe Ser Ser Cys
                965                 970                 975

Val Leu His Phe Cys Glu Glu Leu Glu Glu Phe Trp Val Tyr Arg Ala
                980                 985                 990

Leu Leu Val Glu Leu Thr Lys Lys Leu Thr Tyr Cys Val Lys Ala Glu
                995                1000                1005

Leu Ile Pro Leu Met Glu Val Thr Gly Val Leu Glu Gly Arg Ala
        1010                1015                1020

Lys Gln Leu Tyr Ser Ala Gly Tyr Lys Ser Leu Met His Leu Ala
        1025                1030                1035

Asn Ala Asn Pro Glu Val Leu Val Arg Thr Ile Asp His Leu Ser
        1040                1045                1050

Arg Arg Gln Ala Lys Gln Ile Val Ser Ser Ala Lys Met Leu Leu
        1055                1060                1065

His Glu Lys Ala Glu Ala Leu Gln Glu Glu Val Glu Glu Leu Leu
        1070                1075                1080

Arg Leu Pro Ser Asp Phe Pro Gly Ala Val Ala Ser Ser Thr Asp
        1085                1090                1095

Lys Ala
     1100

<210> SEQ ID NO 6
<211> LENGTH: 121
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (43)..(54)
<223> OTHER INFORMATION: abasic residues
```

```
<220> FEATURE:
<221> NAME/KEY: misc_feature
<222> LOCATION: (76)..(76)
<223> OTHER INFORMATION: hydroxymethylcytosine

<400> SEQUENCE: 6
tttttttttt tttttttttt tttttttttt cccccccccc ccnnnnnnnn nnnnccccccc      60 ccattttcat catccnggtc atttttttttt tttttttttt tggttggtgt ggttggcccc    120
c                                                                     121

<210> SEQ ID NO 7
<211> LENGTH: 121
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (43)..(54)
<223> OTHER INFORMATION: abasic residues
<220> FEATURE:
<221> NAME/KEY: misc_feature
<222> LOCATION: (76)..(76)
<223> OTHER INFORMATION: 5-methylcytosine

<400> SEQUENCE: 7
tttttttttt tttttttttt tttttttttt cccccccccc ccnnnnnnnn nnnnccccccc      60 ccataatcat catccnggtc atttttttttt tttttttttt tggttggtgt ggttggcccc    120
c                                                                     121

<210> SEQ ID NO 8
<211> LENGTH: 44
<212> TYPE: DNA
<213> ORGANISM: Artificial
<220> FEATURE:
<223> OTHER INFORMATION: Synthetically prepared oligonucleotide sequence
<220> FEATURE:
<221> NAME/KEY: misc_feature
<222> LOCATION: (1)..(7)
<223> OTHER INFORMATION: abasic residues

<400> SEQUENCE: 8 nnnnnnnnccc cccccatttt catcatcccg gtcattttttt tttt                      44
```

UNITED STATES PATENT AND TRADEMARK OFFICE
CERTIFICATE OF CORRECTION

PATENT NO. : 11,104,947 B2
APPLICATION NO. : 16/552922
DATED : August 31, 2021
INVENTOR(S) : Rand It is certified that error appears in the above-identified patent and that said Letters Patent is hereby corrected as shown below:

In the Claims

In Column 23, Claim 5, Line 2, please replace "He1308" with --- Hel308 ---; and In Column 23, Claim 11, Line 16, please delete the word "by".

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*